(12) United States Patent
Wang et al.

(10) Patent No.: US 10,709,788 B2
(45) Date of Patent: Jul. 14, 2020

(54) CHITOSAN MAGNETIC PARTICLE DRUG CARRIER, DRUG STRUCTURE, AND METHOD OF MAKING

(71) Applicant: GENE'E TECH CO., LTD., Taipei (TW)

(72) Inventors: Chung-Hao Wang, Taipei (TW); Shu-Jyuan Yang, Taipei (TW); Chien-Ming Lee, Taipei (TW)

(73) Assignee: GENE'E TECH CO., LTD., New Taipei (TW)

( * ) Notice: Subject to any disclaimer, the term of this patent is extended or adjusted under 35 U.S.C. 154(b) by 0 days.

(21) Appl. No.: 16/258,737

(22) Filed: Jan. 28, 2019

(65) Prior Publication Data

US 2020/0114009 A1 Apr. 16, 2020

(30) Foreign Application Priority Data

Oct. 11, 2018 (TW) .............................. 107135760 A

(51) Int. Cl.
| | |
|---|---|
| *A61K 47/36* | (2006.01) |
| *A61K 47/69* | (2017.01) |
| *A61P 31/04* | (2006.01) |
| *A61P 1/04* | (2006.01) |
| *A61K 47/34* | (2017.01) |

(Continued)

(52) U.S. Cl.
CPC .............. *A61K 47/36* (2013.01); *A61K 47/34* (2013.01); *A61K 47/6923* (2017.08); *A61P 1/04* (2018.01); *A61P 31/04* (2018.01); *A61K 31/415* (2013.01); *A61K 31/43* (2013.01); *A61K 31/4439* (2013.01); *A61K 31/573* (2013.01);

(Continued)

(58) Field of Classification Search
CPC .... A61K 47/34; A61K 47/6923; A61K 47/36; A61P 1/04; A61P 31/04; A61P 31/4439; A61P 31/43; A61P 31/573; A61P 31/727; A61P 31/415; A61P 31/717; A61P 31/65
See application file for complete search history.

(56) References Cited

FOREIGN PATENT DOCUMENTS

| TW | 201138788 A | 11/2011 |
|---|---|---|
| TW | I482632 B | 5/2015 |
| TW | I510255 B | 12/2015 |

OTHER PUBLICATIONS

Quinones et al, "Chitosnan Based Self-Assembled Nanoparticles in Drug Delivery", Polymers (Basel), 10(3),:235. (Year: 2018).*

(Continued)

*Primary Examiner* — Carlos A Azpuru

(57) ABSTRACT

A drug carrier, a drug structure, a purpose of the same, a method of making the same, and a method of using the same to inhibit *H. pylori* are revealed. The drug carrier includes a negatively charged polymer, chitosan and magnetic particles. The purpose of the drug carrier is to make a drug for inhibiting *H. pylori*. The drug structure includes a negatively charged polymer, chitosan, magnetic particles and an active ingredient. The method of making the drug structure includes mixing the negatively charged polymer solution, the chitosan solution, the magnetic particles and the active ingredient solution to form an initial solution and allowing ingredients in the initial solution to react and thereby form drug structure particles. The method of using the drug structure to inhibit *H pylori* includes administering the drug structure to an *H. pylori* colony. The drug carrier and drug structure demonstrate enhanced therapeutic efficacy.

15 Claims, 12 Drawing Sheets

(51) Int. Cl.
    *A61K 31/65*           (2006.01)
    *A61K 31/727*         (2006.01)
    *A61K 31/573*         (2006.01)
    *A61K 31/43*           (2006.01)
    *A61K 31/4439*       (2006.01)
    *A61K 31/415*         (2006.01)
    *A61K 31/717*         (2006.01)

(52) U.S. Cl.
    CPC ............ *A61K 31/65* (2013.01); *A61K 31/717*
                    (2013.01); *A61K 31/727* (2013.01)

(56) References Cited

OTHER PUBLICATIONS

Gurmezescu et al, Biocompatible Fe3O4 Increases the Efficacy of Amoxicillin Delivery Against Gram-Positive and Gram-Negatobve Bacteria, Molecules, 19(4), 5013-5027. (Year: 2014).*

* cited by examiner sample 2 sample B sample 3 sample C sample B sample C

A:
in the absence of applied magnetic field for 5 minutes

B:
in the presence of applied magnetic field for 5 minutes

C:
in the absence of applied magnetic field for 10 minutes

D:
in the presence of applied magnetic field for 10 minutes

VL:
visible light

FL:
fluorescent light

VF:
visual field

CHITOSAN MAGNETIC PARTICLE DRUG CARRIER, DRUG STRUCTURE, AND METHOD OF MAKING

CROSS-REFERENCE TO RELATED APPLICATION

This non-provisional application claims priority under 35 U.S.C. § 119(a) on Patent Application No(s).107135760 filed in Taiwan, R.O.C. on Oct. 11, 2018, the entire contents of which are hereby incorporated by reference.

FIELD OF THE INVENTION

The present disclosure relates to a drug carrier, drug structure, purpose of same, method of making same, and method of using same to inhibit *H. pylori* and, more particularly, to a drug carrier to be guided by an applied magnetic field and a drug structure having the drug carrier.

BACKGROUND OF THE INVENTION

*H. pylori* is a bacterium usually found in the stomach and the duodenum. Epidemiological studies confirm that *H. pylori* mainly spreads via contaminated water and foods. The prevalence of *H. pylori* infections among persons aged below 20% in underdeveloped countries and developing countries is as high as 80-90%.

Once a human being is infected with *H. pylori*, *H. pylori* ends up in the epithelium of the stomach. *H. pylori* produces urease which turns a tiny amount of urea existing in the stomach into alkaline ammonia to maintain the neutral environment at the site of *H. pylori* infection, thereby preventing *H. pylori* from being destroyed by gastric acid. Toxins and toxic enzymes produced by *H. pylori* are not only conducive to transfer and reproduction of *H. pylori* but also conducive to survival of *H. pylori*.

*H. pylori* penetrates the mucosal lining of the stomach and thus reaches the neutral environment of the surface of the epithelium of the stomach, thereby damaging the epithelium of the stomach. During the aforesaid process, the epithelium of the stomach releases oxygen free radicals and protease products. The oxygen free radicals and protease products manifest toxicity on the epithelium of the stomach, causing chronic inflammations and digestive tract ulcers (i.e., open sores that develop on the inside lining of the stomach and duodenum). When not treated properly, the digestive tract ulcers may lead to complications, such as digestive tract bleeding, perforations, and gastric outlet obstruction, or even cause stomach cancer.

At present, the standard first-line therapy for *H. pylori* infection is triple therapy and quadruple therapy. At present, antibiotics for inhibiting *H. pylori* include clarithromycin, levofloxacin, metronidazole, tetracycline and amoxicillin. However, at present, the efficacy of the aforesaid therapies is low as a result of poor patient compliance, because of a lengthy therapeutic course for eradication of *H. pylori*, an overly large number (i.e., 10) of capsules to take each time, and side-effects of the aforesaid drugs for treating *H. pylori* infection include dizziness, diarrhea, furry tongue, insensitive to taste, and allergy.

Taiwan patent 1510255 discloses nanoparticles comprising crosslinked glucosamine and amoxicillin, wherein water-in-oil emulsion is formed by the introduction of anionic surfactants and oil, so as to crosslink glucosamine and encapsulate amoxicillin. The nanoparticles have an average particle diameter of 100 to 600 nm, the amoxicillin thus encapsulated accounts for at least 5% (w/w) of the total weight of the nanoparticles. When taken orally, the nanoparticles have longer retention duration in the stomach than free amoxicillin or microscale beads.

Taiwan patent 201138788 discloses a drug structure for treating digestive tract ulcers. The drug structure is formed by encapsulating a drug in algin functioning as a substrate to form a microsphere and then encapsulating the microsphere in a chitosan sheath. According to Taiwan patent 201138788 (the specification, page 7, lines 18-25), the drug structure is slowly released, by forming colloidal algin.

U.S. Pat. No. 6,284,745 discloses a drug structure which requires joint use of algin and chitosan. In the course of making the drug structure, calcium pantothenate is introduced so that sodium alginate for use in making algin forms colloidal beads to make a drug. The drug structure is capable of releasing an included drug instantaneously within two hours.

Taiwan patent 1482632 discloses polymerizing alginate and chitosan to form a drug carrier for use in eradicating *H. pylori*, releasing a drug effectively from the drug carrier in the gastric mucosa environment (pH 7.4) to inhibit the growth of *H. pylori* by the increase of interaction of alginate and chitosan molecules, and allowing the drug carrier to adhere to the gastric mucosa by means of mucoadsive of chitosan to thereby extend the duration of retention of the drug in the gastric mucosa.

The aforesaid patents disclose microsphere drug carriers or microsphere drug structures for inhibiting *H. pylori*. However, unsolved issues include: how to enhance therapeutic efficacy of a drug carrier or a drug structure so as to reduce the dosage of a drug to take each time and lessen the side-effects of the drug.

SUMMARY OF THE INVENTION

It is an objective of the present disclosure to provide a drug carrier, comprising: 90 to 110 parts by weight of a negatively charged polymer; 400 to 1250 parts by weight of chitosan; and 150 to 500 parts by weight of magnetic particles.

Regarding the drug carrier, the negatively charged polymer is of a concentration of 100 parts by weight, the chitosan is of a concentration of 600 to 850 parts by weight, and the magnetic particles are of a concentration of 250 to 350 parts by weight.

Regarding the drug carrier has a particle diameter of 120 to 200 nm.

Regarding the drug carrier, the drug carrier in an aqueous solution has a surface potential of 45 to 49 mV.

Regarding the drug carrier, the negatively charged polymer is one selected from the group consisting of alginate, heparin, polyacrylic acid, poly (methacrylic acid) and carboxymethyl cellulose.

In order to achieve the above and other objectives, the present disclosure provides a drug carrier for use in making a drug for inhibiting *H. pylori*, and its purposes comprises the drug carrier.

In order to achieve the above and other objectives, the present disclosure provides a method of making a drug carrier, comprising steps of: (a) providing 90 to 110 parts by weight of a negatively charged polymer solution, 400 to 1250 parts by weight of a chitosan solution and 150 to 500 parts by weight of magnetic particles; (b) mixing the negatively charged polymer solution, the chitosan solution and the magnetic particles to form an initial solution; and (c) stirring the initial solution for at least 10 minutes to form drug carrier particles.

Regarding the method, the negatively charged polymer is of a concentration of 100 parts by weight, the chitosan is of a concentration of 600 to 850 parts by weight, and the magnetic particles are of a concentration of 250 to 350 parts by weight.

In order to achieve the above and other objectives, the present disclosure provides a drug structure, comprising: 90 to 110 parts by weight of a negatively charged polymer; 400 to 1250 parts by weight of chitosan; 150 to 500 parts by weight of magnetic particles; and 500 to 1500 parts by weight of an active ingredient having activity of inhibiting *H. pylori*.

Regarding the drug structure, the negatively charged polymer is of a concentration of 100 parts by weight, the chitosan is of a concentration of 600 to 850 parts by weight, the magnetic particles are of a concentration of 250 to 350 parts by weight, and the active ingredient is of a concentration of 750 to 1000 parts by weight.

Regarding the drug structure, the drug structure has a particle diameter of 137 to 210 nm.

Regarding the drug structure, the active ingredient in the drug structure has a encapsulation efficiency of 72.6 to 79.2%.

Regarding the drug structure, the active ingredient in the drug structure accounts for 30 to 45% (w/w) of a total weight of the drug structure.

Regarding the drug structure, the drug structure in an aqueous solution has a surface potential of 44 to 48 mV.

Regarding the drug structure, the negatively charged polymer is one selected from the group consisting of alginate, heparin, polyacrylic acid, poly (methacrylic acid) and carboxymethyl cellulose.

Regarding the drug structure, the active ingredient is one selected from the group consisting of amoxicillin, clarithromycin, omeprazole, levofloxacin, metronidazole and tetracycline.

In order to achieve the above and other objectives, the present disclosure provides a method of making a drug structure, comprising steps of: (a) providing 90 to 110 parts by weight of a negatively charged polymer solution, 400 to 1250 parts by weight of a chitosan solution, 150 to 500 parts by weight of magnetic particles and 500 to 1500 parts by weight of an active ingredient solution; (b) mixing the negatively charged polymer solution, the chitosan solution, the magnetic particles and the active ingredient solution to form an initial solution; and (c) stirring the initial solution for at least 10 minutes to form drug structure particles.

Regarding the method, the negatively charged polymer is of a concentration of 100 parts by weight, the chitosan is of a concentration of 600 to 850 parts by weight, the magnetic particles are of a concentration of 250 to 350 parts by weight, and the active ingredient is of a concentration of 750 to 1000 parts by weight.

In order to achieve the above and other objectives, the present disclosure provides a method of inhibiting *H. pylori*, comprising steps of: (a) providing the drug structure; and (b) administering an effective dose of the drug structure to an *H. pylori* colony.

Regarding the aforesaid method, further comprising a step (c) of providing an applied magnetic field and applying it to the drug structure.

The drug carrier and the drug structure are provided with a view to enhancing therapeutic efficacy of the drug carrier and the drug structure so as to reduce the dosage of a drug to take each time and lessen the side-effects of the drug.

DETAILED DESCRIPTION OF THE PREFERRED EMBODIMENTS

Figure 1:
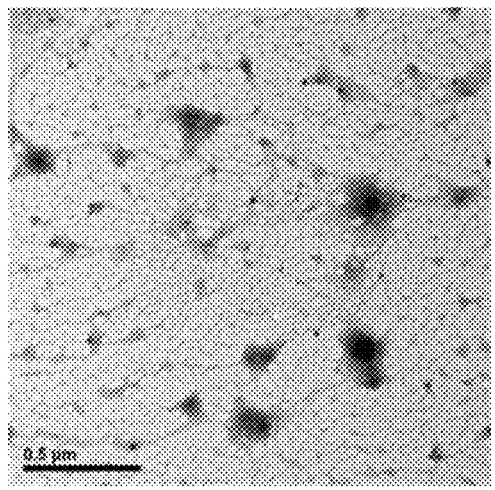
FIG. 1 shows pictures taken of surfaces of a drug carrier and surfaces of a drug structure under a transmission electron microscope (TEM)
Figure 1:
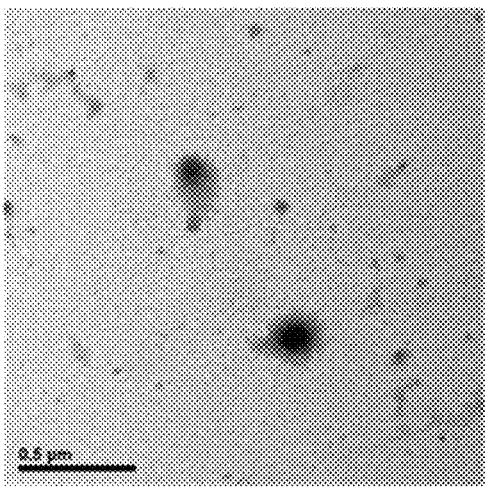
Figure 1:
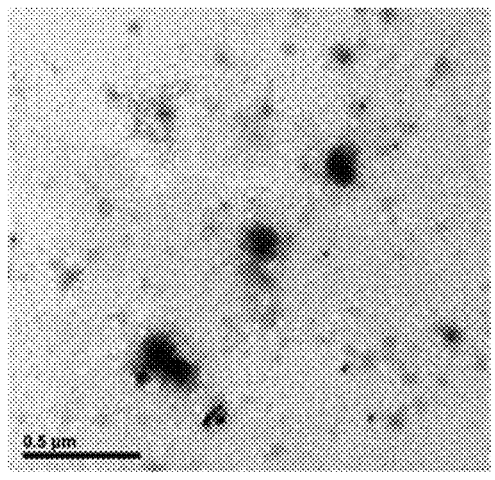
Figure 1:
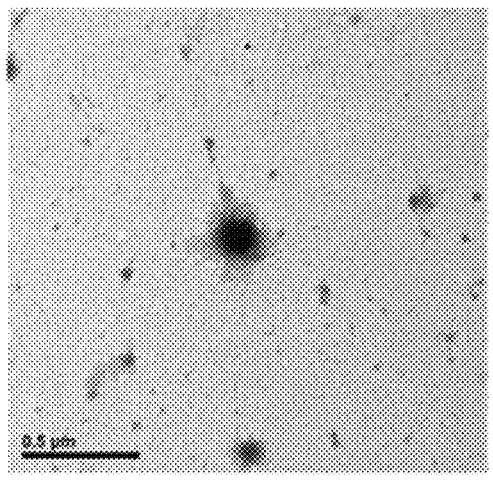

Objectives, features, and advantages of the present disclosure are hereunder illustrated with specific embodiments, depicted with accompanying drawings, and described below.

Drug Carrier Making Method

A method of making a drug carrier is described below.

First, providing 90 to 110 parts by weight of a negatively charged polymer, 400 to 1250 parts by weight of chitosan and 150 to 500 parts by weight of magnetic particles. The negatively charged polymer is one selected from the group consisting of alginate, heparin, polyacrylic acid, poly (methacrylic acid) and carboxymethyl cellulose. Both the negatively charged polymer and the chitosan are provided in the form of a solution. The magnetic particles are selectively dissolved in a solution or not dissolved in a solution. The negatively charged polymer, chitosan and magnetic particles, provided in the form of solutions, are conducive to controlling the pH values of the aforesaid ingredients, thereby allowing the ingredient to stay in an appropriately charged state.

Afterward, the negatively charged polymer solution, chitosan solution and magnetic particles are stirred or treated with any other means of mixing, so as to be mixed uniformly to form an initial solution. Being a solution, the initial solution enables the ingredients in the drug carrier to maintain the appropriately charged state, so as to maintain the structure of the drug carrier.

Finally, the initial solution is stirred at 25° C. for 10 minutes or more (for example, 15 minutes, 20 minutes) such that, owing to their charged characteristics, the negatively charged polymer, the chitosan and the magnetic particles in the initial solution are attracted to each other by generating static electricity, and thus they are coupled to each other to form drug carrier particles, thereby forming a solution containing the drug carriers.

With the drug carrier functioning as a carrier for a drug or active substance, the active substance or drug can be simultaneously added to the initial solution of the drug carrier in the course of making the drug carrier such that the drug carrier encapsulate the active substance or drug when forming particles or the solution containing the drug carrier particles and a solution containing an active substance or drug are mixed such that the active substance or drug adheres to the outer surfaces of the drug carrier particles, thereby allowing the drug carrier to carry the drug or active substance. The drug carrier particles which encapsulate the active substance or drug is regarded as a drug structure. The method of making the drug structure is described later.

Regarding the method of making the drug carrier, the negatively charged polymer is of a concentration of 95 to 105 parts by weight, the chitosan is of a concentration of 600 to 850 parts by weight, and the magnetic particles are of a concentration of 250 to 350 parts by weight.

The materials which the drug carrier is made of are mixed sequentially. First, the chitosan solution and the magnetic particles are mixed to form a chitosan-magnetic particles solution. Then, the chitosan-magnetic particles solution and the negatively charged polymer solution are mixed. In another embodiment, the chitosan solution, the magnetic particles and the negatively charged polymer solution are mixed simultaneously or mixed in another order, without being limited to this embodiment. Furthermore, in this embodiment, the magnetic particles are provided in the form of a ferric oxide solution. However, in another embodiment, the magnetic particles are provided in the form of another solution or are not dissolved in a solution.

In this embodiment, the solution containing the drug carriers has a pH value of 3-5.5, and preferably 4-4.5. However, in another embodiment, the pH value of the solution containing the drug carriers changes with the pH values of the chitosan solution, negatively charged polymer solution, and ferric oxide solution during the initial reaction, without being limited to this embodiment.

In this embodiment, the chitosan solution has a pH value of 2.5-5 and preferably 3.5-4, the ferric oxide solution has a pH value of 2.5-5 and preferably 3.5-4, and the negatively charged polymer solution has a pH value of 6-8 preferably 7.4-8.0. However, in another embodiment, the pH values of the chitosan solution, the ferric oxide solution and the negatively charged polymer solution are adjusted as needed, without being limited to this embodiment.

In this embodiment, the drug carrier is for making a drug for inhibiting *H. pylori*, for functioning as a drug for inhibiting *H. pylori*, or has an active substance. However, in another embodiment, the drug carrier is for making a drug for inhibiting another bacterium or treating another disease, for functioning as a drug for inhibiting another bacterium or treating another disease, or has an active substance, and thus is not limited to this embodiment.

In this embodiment, the negatively charged polymer relates to a polymer negatively charged in neutral and acidic environments and, more particularly, to a polymer negatively charged in an environment of a pH value of 1-8 approximately, and preferably a polymer negatively charged in an environment of a pH value of 2-8 approximately. The negatively charged polymer includes but is not limited to alginate, heparin, polyacrylic acid, poly (methacrylic acid) and carboxymethyl cellulose.

In this embodiment, chitin is treated with a high-concentration, hot alkali in order to undergo deacetylation so that the acetyl group in chitin turns into an amino group, so as to form chitosan. However, another embodiment employs another chitosan obtained according to the prior art available to persons skilled in the art, without being limited to this embodiment. In this embodiment, the chitosan in use has a molecular weight of around 15,000 Da, and its deacetylation rate is 84%. However, in another embodiment, the chitosan in use has a molecular weight of 12,000 Da to 18,000 Da or a molecular weight of any other value range, whereas its deacetylation rate is 60-90% or a deacetylation rate of any other value range, without being limited to this embodiment. In an acidic environment, the chitosan molecules are positively charged and are mucoadsive and thus are widely applicable to medicine and pharmacy. In addition, the chitosan molecules have highly reactive amino groups and hydroxyl groups; hence, the chitosan molecules are not only used in making another derivatives but are also dissolved in a weak acidic aqueous solution. Therefore, the chitosan molecules are provided in the form of film, balls, fiber or gel as needed. Moreover, chitosan does not bring about allergy and rejection; hence, chitosan is biocompatible with biological tissue. Chitosan undergoes an enzymatic reaction and degrades to form products which are nontoxic amino sugars and thus can be fully absorbed by the human body without causing any side-effects.

In this embodiment, magnetic particles are substance particles having magnetism. The substance having magnetism can be magnetized with an applied magnetic field and guided by the applied magnetic field. The substance having magnetism is exemplified by an iron-containing substance, including but not limited to ferric oxide (magnetite) particles, cobalt-containing ferric oxide particles (Co-doped magnetite particles), manganese-containing ferric oxide (Mn-doped magnetite particles) or nickel-containing ferric oxide (Ni-Doped Magnetite Particles).

Drug Carrier Sample Making

The physical and chemical properties of the drug carrier particles are the same as those of their counterparts in the method of making the drug carrier and the method of making drug carrier samples 1-5. The specific making process is described below.

First, obtain 0.5 mg/ml chitosan solution (dissolved in 0.01M acetic acid; pH=4.0), 1.0 mg/ml polyacrylic acid solution (dissolved in 0.01N sodium hydroxide; pH=7.4) and 0.2 mg/ml ferric oxide solution (dissolved in 0.01M acetic acid; pH=4.0). The solvents for the aforesaid ingredient solutions, solution concentrations and solution pH values only illustrate a preferred embodiment. Another embodiment provides: the chitosan solution of a concentration of 0.3 to 0.7 mg/ml and a pH value of around 3-5; the polyacrylic acid solution of a concentration of 0.8 to 1.2 mg/ml and a pH value of 7-8.5; the ferric oxide solution of a concentration of 0.1 to 0.4 mg/ml and a pH value of 3-5. Furthermore, persons skilled in the art may adjust or alter the solvents of the ingredient solutions, solution concentrations and solution pH values as needed. For example, the chitosan and ferric oxide are dissolved in hydrochloric acid (0.01M; pH=2.0), and polyacrylic acid is dissolved in potassium hydroxide (0.01M; pH=8), so as to be added through a burette to each of the ingredient solutions of a pH range by acid-base titration, without being limited to this embodiment.

Afterward, the chitosan solution, polyacrylic acid solution and ferric oxide solution required for drug carrier samples 1-5 are prepared according to the weight percent of the ingredients in the drug carriers of samples 1-5 shown in Table 1. Sample 1 comprises 1250 parts by weight of chitosan, 100 parts by weight of polyacrylic acid and 500 parts by weight of ferric oxide. Sample 2 comprises 830 parts by weight of chitosan, 100 parts by weight of polyacrylic acid and 330 parts by weight of ferric oxide. Sample 3 comprises 630 parts by weight of chitosan, 100 parts by weight of polyacrylic acid and 250 parts by weight of ferric oxide. Sample 4 comprises 500 parts by weight of chitosan, 100 parts by weight of polyacrylic acid and 200 parts by weight of ferric oxide. Sample 5 comprises 420 parts by weight of chitosan, 100 parts by weight of polyacrylic acid and 170 parts by weight of ferric oxide.

Referring to the aforesaid drug carrier making method, the chitosan solution and ferric oxide solution in each sample are mixed to form a chitosan-ferric oxide solution, then the chitosan-ferric oxide solution and polyacrylic acid solution in each sample are mixed to react with each other to thereby form a solution containing the drug carriers, so as to obtain the drug carrier samples 1-5.

TABLE 1 weight percent of ingredients of drug carrier samples 1-5

| sample | chitosan | polyacrylic acid | ferric oxide |
|---|---|---|---|
| 1 | 12.5 | 1 | 5 |
| 2 | 8.3 | 1 | 3.3 |
| 3 | 6.3 | 1 | 2.5 |
| 4 | 5 | 1 | 2 |
| 5 | 4.2 | 1 | 1.7 |

Table 2 below shows the average particle diameter, polydisperse Index (PDI), and surface potential of the drug carrier samples 1-5 in this embodiment.

| sample | average particle diameter (nm) | PDI | surface potential (mV) |
|---|---|---|---|
| 1 | 126.8 ± 7.29 | 0.507 | 46.7 ± 1.72 |
| 2 | 142.4 ± 2.33 | 0.386 | 48.0 ± 0.99 |
| 3 | 150.4 ± 1.64 | 0.338 | 48.2 ± 1.45 |
| 4 | 177.6 ± 5.54 | 0.300 | 48.5 ± 1.71 |
| 5 | 187.7 ± 7.36 | 0.320 | 48.1 ± 1.18 |

As shown in Table 2 above, the particle diameters of the drug carriers in this embodiment are around 120 to 200 nm, preferably 140 to 150 nm, and the size of the drug carriers is conducive to enhancement of absorption of the drug carriers inside the human body. The drug carriers in an aqueous solution have a surface potential of 45 to 49 mV, preferably 45 to 48 mV. The surface potential is conducive to extension of the duration of retention of the drug structures in the stomach. Furthermore, the PDI data related to the drug carriers and shown in Table 2 indicates that the particle diameters of the drug carriers are narrowly distributed and thus manifest satisfactory homogeneity.

Method of Making Drug Structure

The drug structure is made by the following method.

First, provide 90-110 parts by weight of a negatively charged polymer, 400 to 1250 parts by weight of chitosan, 150 to 500 parts by weight of magnetic particles and 500 to 1500 parts by weight of an active ingredient. The negatively charged polymer, the chitosan and the active ingredient are provided in the form of a solution. The magnetic particles are selectively dissolved in a solution or not dissolved in a solution. The negatively charged polymer, chitosan, magnetic particles and active ingredient are provided in the form of a solution and thus are conducive to controlling the pH values of the aforesaid ingredients such that the ingredients are in an appropriately charged state.

Afterward, the negatively charged polymer solution, chitosan solution, magnetic particles and active ingredient solution are stirred or treated with any other means of mixing to mix uniformly to form an initial solution. Being a solution, the initial solution enables the ingredients in the drug structure to maintain the appropriately charged state, so as to maintain the structure of the drug structure.

Finally, the initial solution is stirred at 25° C. to react for 10 minutes such that the negatively charged polymer, the chitosan, the magnetic particles and the active ingredient in the initial solution are attracted to each other by generating static electricity, and thus they are coupled to each other to form the drug structure, thereby forming a solution containing the drug structure.

In this embodiment, the reactant, the negatively charged polymer, the chitosan and the magnetic particles for use in the method of making the drug structure are the reactants for use in the method of making the drug carrier. Hence, in this embodiment, the drug structure comprises the drug carrier ingredient and the active ingredient. The drug carrier functions as the carrier for the active ingredient.

Since the drug carrier and drug structure in this embodiment are not core-shell structure and the magnetic substances are uniformly distributed in the drug structure. Therefore, in this embodiment, the method of making the drug carrier and drug structure is a solution-based method rather than water-in-oil emulsion method; hence, the ingredient solutions are uniformly mixed. In this embodiment, the ingredients in the drug carrier and drug structure are charged and thus attracted to each other by generating static electricity, so as to make the drug carrier and drug structure in this embodiment. Compared with conventional methods of making core-shell drug carriers and drug structures, the method of making the drug carrier and drug structure in this embodiment dispenses with a surfactant and oil in order to form an emulsion agent. Hence, in this embodiment, the method of making the drug carrier and drug structure is easier than conventional methods of making core-shell drug carriers and drug structures. Furthermore, the drug structure obtained by the method of making the drug structure in this embodiment has higher active ingredient encapsulation efficiency than conventional drug structures.

In this embodiment, the negatively charged polymer, the chitosan and the magnetic particles for use in the method of making the drug structure preferably correspond in parts by weight to the ingredients for use in the method of making the drug carrier, respectively, wherein the active ingredient is preferably of a concentration of 750 to 1000 parts by weight.

In this embodiment, reactants for use in making the drug structure are mixed sequentially. First, the negatively charged polymer solution and the active ingredient solution are mixed to form the first pre-mix solution. Then, the chitosan solution and the magnetic particles are mixed to form the second pre-mix solution. Finally, the first pre-mix solution and the second pre-mix solution are mixed to form the initial solution. However, in another embodiment, the chitosan solution, the magnetic particles, the negatively charged polymer solution and the active ingredient solution are mixed simultaneously or mixed in another order, without being limited to this embodiment. In this embodiment, the magnetic particles take on ferric oxide solution surface appearance. However, in another embodiment, the magnetic particles also take on another solution surface appearance or is not dissolved in a solution.

In this embodiment, the chitosan solution, the ferric oxide solution and the negatively charged polymer solution for use in the method of making the drug structure corresponding in pH to the ingredients for use in the method of making the drug carrier, respectively, wherein the active ingredient solution is of a pH 6.5-8.5, preferably 7.4-8.0. However, in another embodiment, the pH values of the chitosan solution, the ferric oxide solution, the negatively charged polymer solution and the active ingredient solution are adjusted as needed, without being limited to this embodiment.

The active ingredient is defined as a compound that serves therapeutic, preventive and evaluative purposes. However, in this embodiment, the active ingredient is further defined as a substance having activity of inhibiting *H.pylori*, comprising amoxicillin, clarithromycin, omeprazole, levofloxacin, metronidazole or tetracycline.

In this embodiment, from a macro perspective, the activity of inhibiting *H. pylori* is the activity of controlling the size of an *H. pylori* colony, reducing an *H. pylori* colony, and/or causing an *H. pylori* colony to vanish, whereas, from a micro perspective, the activity of inhibiting *H. pylori* is the activity of reducing the physiologic activity of an *H. pylori* individual, reducing infection capability of an *H. pylori* individual, and/or eradicating an *H. pylori* individual.

Drug Structure Sample Making

In this embodiment, the drug structure samples A-E are made according to the aforesaid drug structure making method, and the specific making process is described below.

First, obtain 0.5 mg/ml chitosan solution (dissolved in 0.01M acetic acid; pH=4.0), 1.0 mg/ml polyacrylic acid solution (dissolved in 0.01N sodium hydroxide; pH=7.4), 0.2 mg/ml ferric oxide solution (dissolved in 0.01M acetic acid; pH=4.0), and 1.5 mg/ml amoxicillin solution (dissolved in 0.01N sodium hydroxide; pH=7.4) functioning as an active ingredient. In another embodiment, the range of concentrations and the range of pH values of the chitosan solution, the polyacrylic acid solution and the ferric oxide solution depend on the requirements of corresponding ingredient solutions in the course of making the drug carrier samples, setting the range of concentration of the amoxicillin solution to 1-2 mg/ml and the range of pH value of the amoxicillin solution to around pH 6.5-8.5. Solvents of the ingredient solutions, solution concentrations and solution pH values are described herein merely to illustrate a preferred embodiment, but persons skilled in the art may adjust or alter the solvents of the ingredient solutions, solution concentrations and solution pH values as needed in accordance with the aforesaid course of making the drug carrier samples, without being limited to this embodiment.

The chitosan solution, polyacrylic acid solution, ferric oxide solution and amoxicillin solution required for drug structure samples A-E, respectively, are prepared in accordance with weight proportions of the ingredients in the drug structure of samples A-E shown in Table 3. Sample A comprises 1250 parts by weight of chitosan, 100 parts by weight of polyacrylic acid, 500 parts by weight of ferric oxide and 1500 parts by weight of amoxicillin. Sample B comprises 830 parts by weight of chitosan, 100 parts by weight of polyacrylic acid, 330 parts by weight of ferric oxide and 1000 parts by weight of amoxicillin. Sample C comprises 630 parts by weight of chitosan, 100 parts by weight of polyacrylic acid, 250 parts by weight of ferric oxide and 750 parts by weight of amoxicillin. Sample D comprises 500 parts by weight of chitosan, 100 parts by weight of polyacrylic acid, 200 parts by weight of ferric oxide and 600 parts by weight of amoxicillin. Sample E comprises 420 parts by weight of chitosan, 100 parts by weight of polyacrylic acid, 170 parts by weight of ferric oxide and 500 parts by weight of amoxicillin.

Referring to the method of making the drug structure, polyacrylic acid solution and amoxicillin solution in the samples are mixed to form a first pre-mix solution, then the chitosan solution and ferric oxide solution in each sample are mixed to form a second pre-mix solution, and finally the first pre-mix solution and second pre-mix solution in each sample are mixed to form the initial solution. Afterward, the initial solution is stirred to react for 10 minutes and thereby form a solution containing the drug structure, thereby obtaining the drug structure samples A-E.

TABLE 3 weight percent of ingredients of drug structure samples A-E

| sample | chitosan | polyacrylic acid | ferric oxide | amoxicillin |
|---|---|---|---|---|
| A | 12.5 | 1 | 5 | 15 |
| B | 8.3 | 1 | 3.3 | 10 |
| C | 6.3 | 1 | 2.5 | 7.5 |
| D | 5 | 1 | 2 | 6 |
| E | 4.2 | 1 | 1.7 | 5 |

Table 4 below shows average particle diameter, PDI, and surface potential of drug structure samples A-E in this embodiment.

| sample | average particle diameter (nm) | PDI | surface potential (mV) | encapsulation efficiency |
|---|---|---|---|---|
| A | 139.5 ± 2.50 | 0.488 | 45.0 ± 0.96 | 72.7 ± 0.10 |
| B | 151.9 ± 7.92 | 0.375 | 45.9 ± 1.22 | 75.5 ± 0.44 |
| C | 167.3 ± 4.57 | 0.303 | 46.5 ± 1.05 | 77.8 ± 0.63 |
| D | 189.0 ± 1.83 | 0.32 | 46.3 ± 0.65 | 78.8 ± 1.61 |
| E | 201.8 ± 7.57 | 0.337 | 47.5 ± 0.68 | 79.1 ± 0.09 |

Table 4 above shows that, in this embodiment, particle diameters of the drug structures are around 137 to 210 nm, preferably 150 to 170 nm. The size of the drug structures is conducive to enhancement of the efficiency of absorption of the drug structures inside the human body. In this embodiment, the active ingredient encapsulation efficiency of the drug structure is around 72.6 to 79.2%, preferably 75 to 78%. The active ingredient encapsulated in the drug structure accounts for 30 to 45% (w/w), preferably 35 to 40% (w/w), and most preferably 37 to 38% (w/w), of the total weight of the drug structure. The drug structure in an aqueous solution has a surface potential of 44 to 48 mV, preferably 45 to 47 mV. The surface potential is conducive to extension of the duration of retention of the drug structure in the stomach. Furthermore, the PDI data related to the drug structure and shown in Table 4 indicates that the particle diameters of the drug structure are narrowly distributed and thus manifest satisfactory homogeneity.

Analysis of Surface Appearance of Drug Carrier Sample and Drug Structure Sample

FIG. 1 shows pictures taken of surfaces of drug carrier samples 2, 3 and surfaces of drug structure samples B, C under a transmission electron microscope (TEM). The drug carrier samples 2, 3 are similar to the drug structure samples B, C in terms of surface appearance of particle aggregation; hence, it can be inferred that in this embodiment the drug carrier and drug structure are similar in terms of physical properties. Furthermore, as shown in FIG. 1, in this embodiment the drug carrier samples and drug structure samples are nanoscale particles. Conventional nanoscale drug carrier particles and drug structure particles manifest satisfactory mucosa penetrability and satisfactory absorption efficiency in the human body; hence, it can be expected that in this embodiment the drug carrier samples and drug structure samples also manifest satisfactory mucosa penetrability and satisfactory absorption efficiency in the human body.

Test of Magnetic Field Guide of Drug Structure

First, a solution containing drug structure samples B, C is prepared by the drug structure sample making method, and then the solution containing the drug structure samples B, C is introduced into a glass flask. Afterward, a magnet is attached to the side wall of the glass flask containing the solution of samples B, C, so as to observe the change in the distribution and positions of samples B, C being attracted to the magnet side in the glass flask. The test simulates how the drug structure samples B, C are guided by an applied magnetic field when located at the head of the stomach of the human body.

Figure 2:
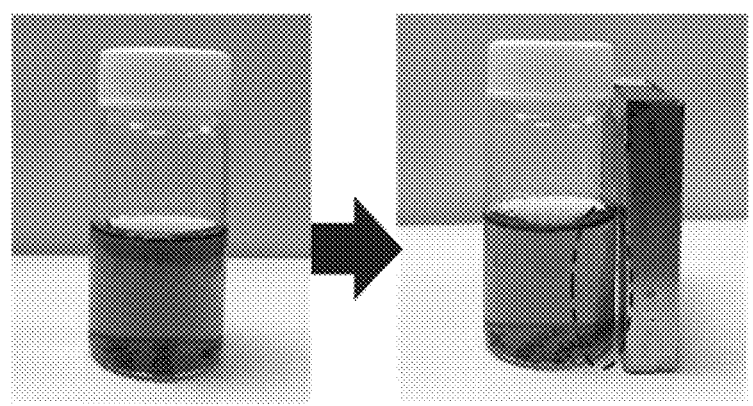
FIG. 2 shows pictures taken of the drug structure moving under guidance of a magnetic field.
Figure 2:
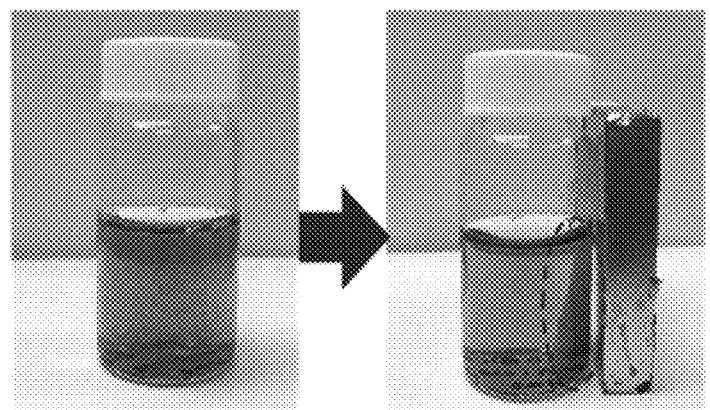

FIG. 2 shows how the drug structure moves under the guidance of a magnetic field. When guided by an external magnet, the drug structure samples B, C contain therein magnetic particles and thus are attracted to the external magnet to therefore move toward the flask wall which the magnet is attached thereto. As shown in FIG. 2, drug structure sample C is most susceptible to the guidance of the magnetic field. Hence, considering the aforesaid test result, it can be inferred that the drug structure in this embodiment can be guided by an applied magnetic field, and thus the duration of retention of the drug structure at a specific position in the stomach of a human body can be extended, thereby enhancing the release of a drug of the drug structure. In addition, the drug structure approaches the site of aggregation of pathogens under the guidance of the applied magnetic field. For example, after a patient has taken the drug structure and the drug structure has entered the stomach of the human body, an electromagnetic field is applied to guide the drug structure so that the drug structure is retained in the inside lining of the stomach for a specific time period or to guide the drug structure so that the drug structure approaches the inside lining of the stomach or gastric mucosa, where the pathogens aggregate.

In this embodiment, the therapeutic efficacy of the drug structure is enhanced, so as to reduce the dosage of a drug to take each time and lessen the side-effects of the drug.

Characteristics of the drug structure particles in different pH environments are tested and described below.

First, a solution containing drug structure samples B, C is prepared according to the method of making the drug structure samples. Then, the solution containing drug structure samples B, C is introduced to five containers. The pH values of the five solutions containing drug structure sample B are set to 2.5, 4.0, 5.0, 6.0 and 7.4, respectively, whereas the pH values of the five solutions containing drug structure sample C are set to 2.5, 4.0, 5.0, 6.0 and 7.4, respectively, to define the different positions of the drug structure in the stomach and their respective pH values, namely gastric acid environment (pH 2.5), different mucosal layer depth environments (pH 4.0-6.0) and the inside lining (pH 7.4) of the stomach. Afterward, experimental samples are extracted from the five solutions containing drug structure sample B and the five solutions containing drug structure sample C, respectively. Then, average particle aggregate size, surface potential, and distribution surface appearance of samples B, C in different pH environments are observed under a nanoparticle diameter and electric potential analyzer (Zetasizer NANO-ZS90) and a transmission electron microscope (TEM).

Figure 3:
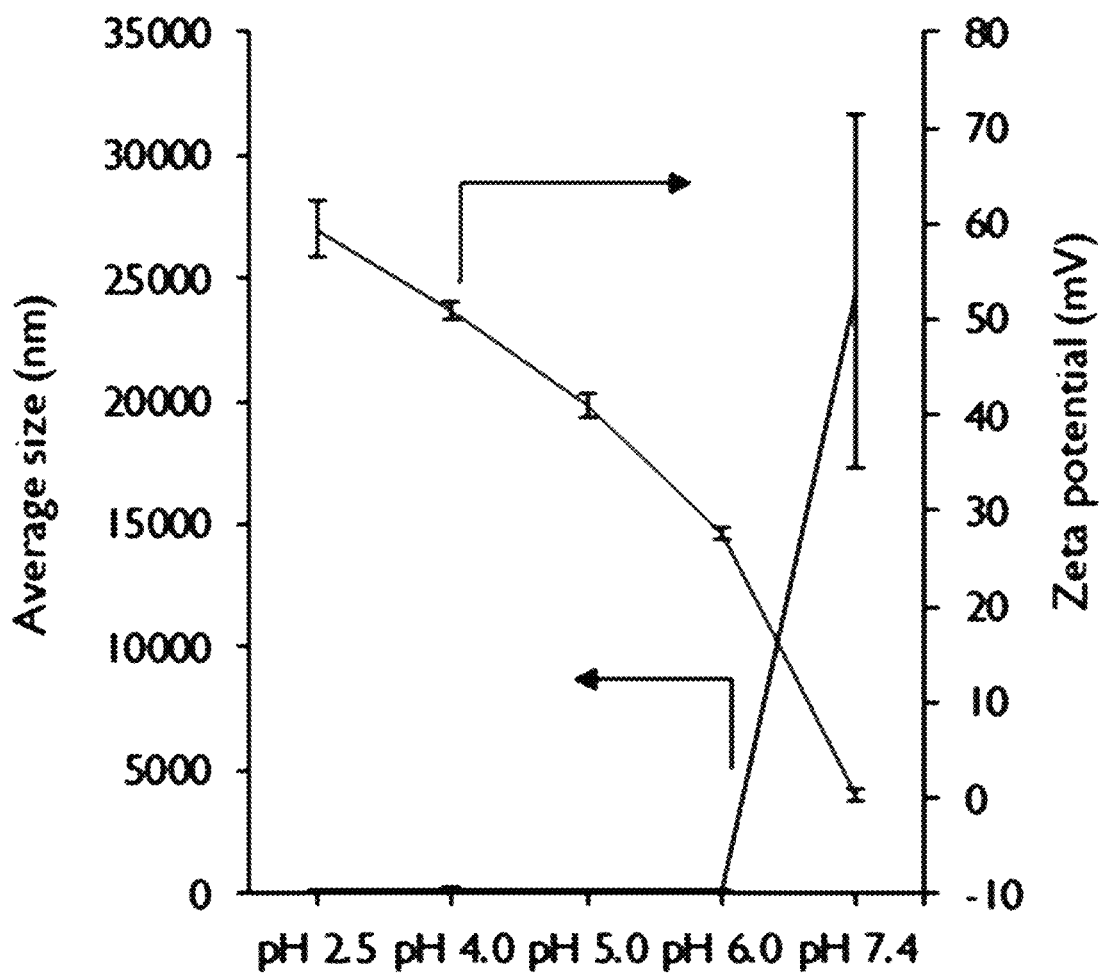
FIG. 3 shows graphs of the drug structure's average particle aggregate size and surface potential against pH.
Figure 4:
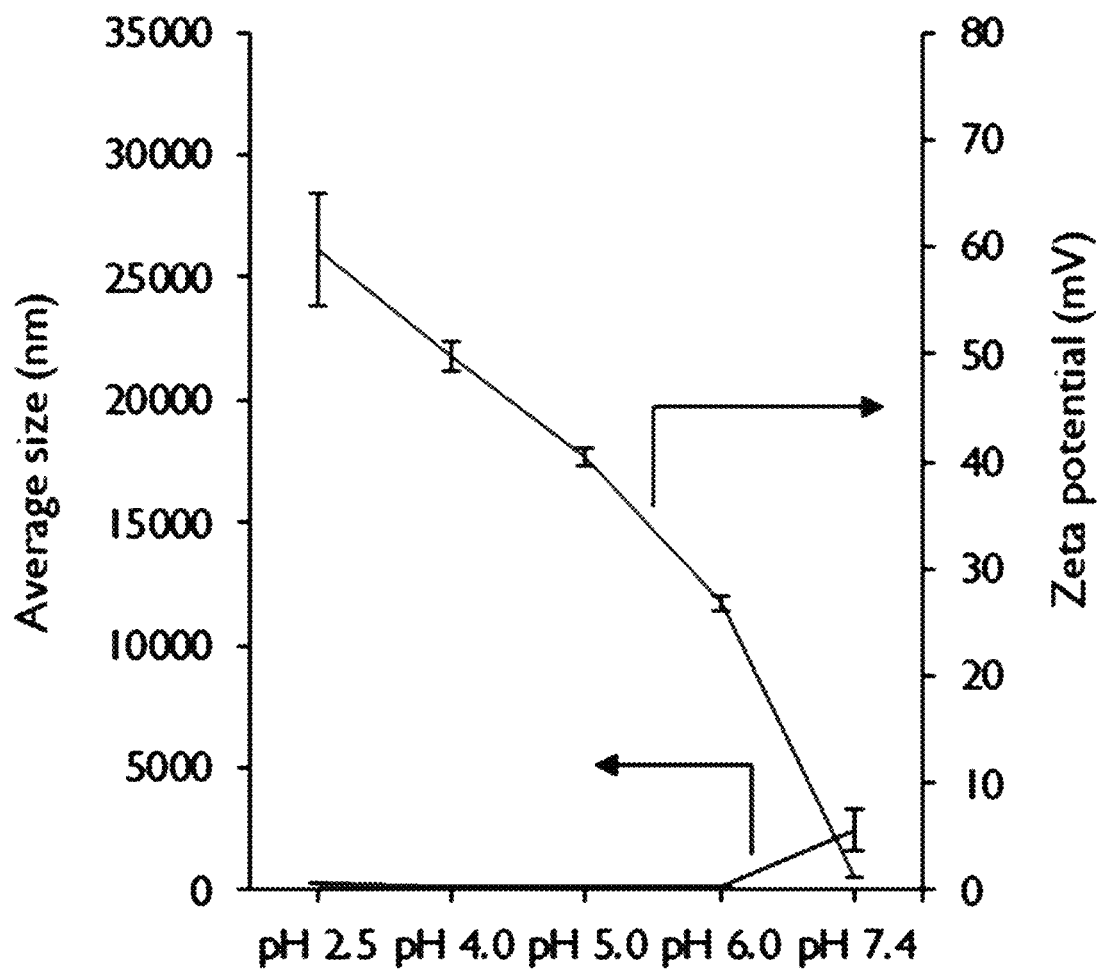
FIG. 4 shows graphs of another drug structure's average particle aggregate size and surface potential against pH.

Referring to FIG. 3 and FIG. 4, there are shown in FIG. 3 graphs of sample B's average particle aggregate size and surface potential against pH, and there are shown in FIG. 4 graphs of sample C's average particle aggregate size and surface potential against pH.

Referring to FIG. 3 and FIG. 4, in an environment of pH 2.5 (equivalent to the gastric acid environment in the human body), the gastric acid fails to erode and damage samples B, C, and thus the surfaces of samples B, C still carry positive charges of 60 mV approximately.

Furthermore, since the chitosan and polyacrylic acid contained in samples B, C are intrinsically capable of adhering to any mucous tissue, the drug structure in the stomach tends to adhere to mucous tissue of the inside lining of the stomach. Depending on its depth, the mucous tissue of the inside lining of the stomach has pH values of 4.0, 5.0 and 6.0 approximately. Referring to FIG. 3 and FIG. 4, when samples B, C are in an environment of pH 4.0-6.0, the surfaces of samples B, C still carry positive charges of 30-50 mV approximately. In an environment of pH 7.4 (equivalent to the stomach's inside lining environment in the human body), that is, a neutral environment, the chitosan does not carry any electrical charges, and thus the surface potential of samples B, C approaches 0 mV.

Figure 5:
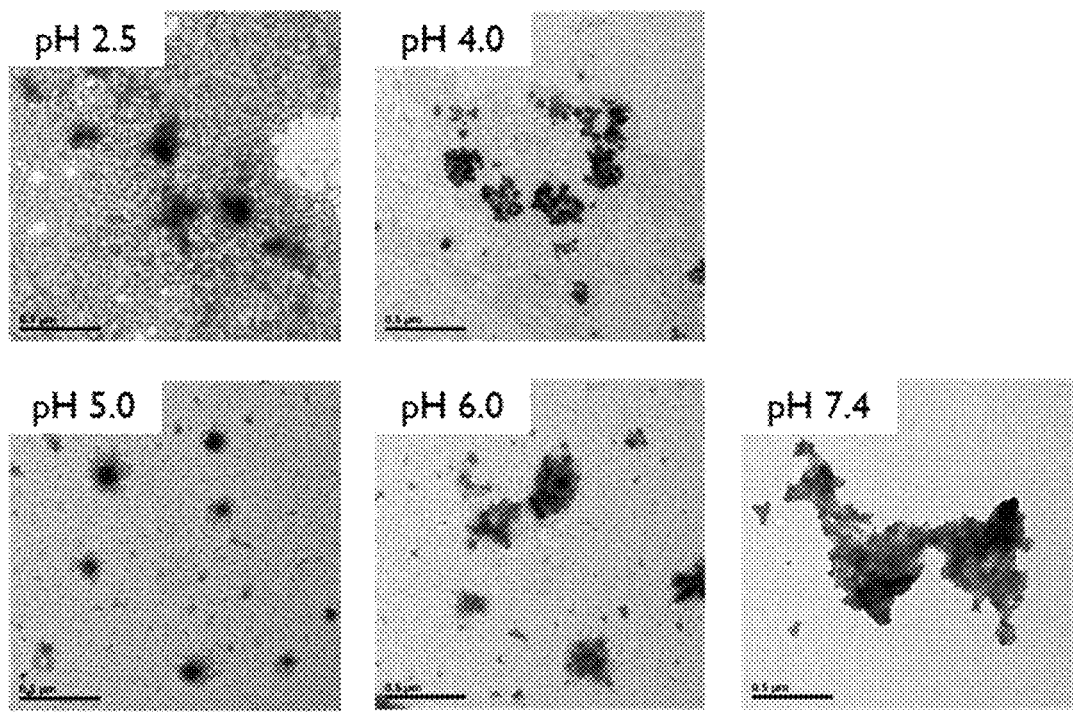
FIG. 5 shows pictures taken of distribution of the drug structure at different pH values.
Figure 6:
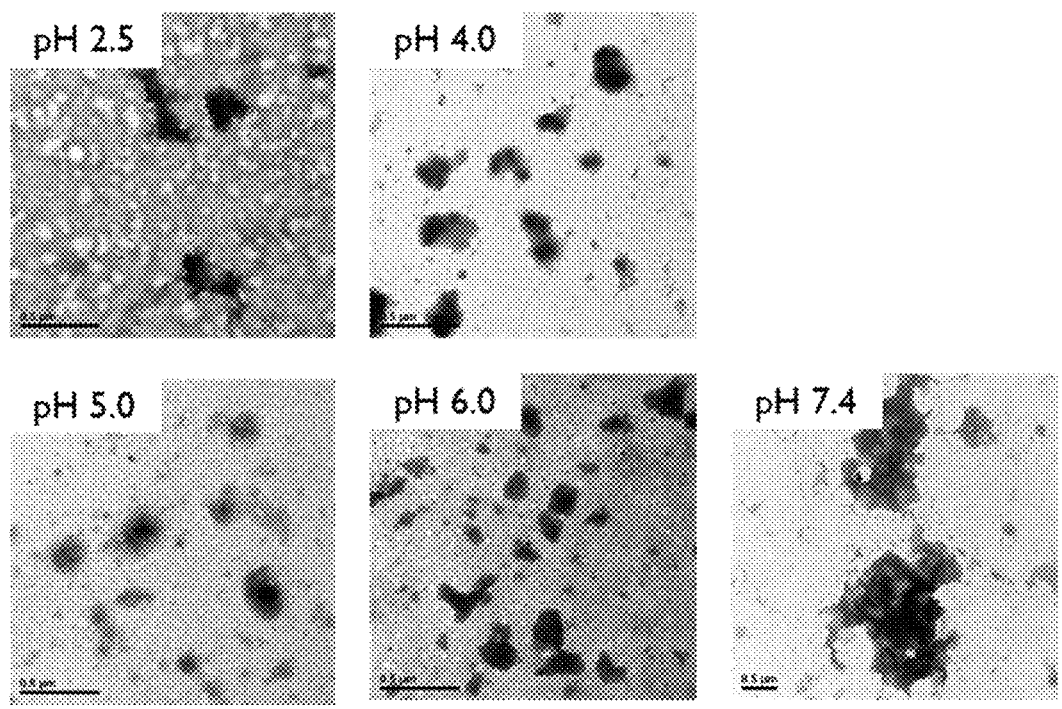
FIG. 6 shows pictures taken of distribution of another drug structure at different pH values.

Referring to FIG. 5 and FIG. 6, there are shown in FIG. 5 pictures taken of distribution of sample B at different pH values, and there are shown in FIG. 6 pictures taken of distribution of sample C at different pH values. As described before, given an environment of a neutral pH value, chitosan enters an uncharged state; hence, the samples B, C enter a dispersed state when located in a pH 2.5 environment and enter an aggregated state when located in a neutral pH environment. Referring to FIG. 3 and FIG. 4, as the pH value of the environment where samples B, C are located at increases from 2.5 to 7.4, average size of the aggregated particles of samples B, C increases from nanoscale to around 25 μm.

As shown by the aforesaid test results, when the drug structure adheres to the mucous tissue and approaches the neutral environment of the inside lining of the stomach, the charged characteristics of the chitosan and polyacrylic acid change; as a result, the drug structure decomposes gradually, thereby releasing the active ingredient from the drug structure. Owing to the aforesaid characteristics of the drug structure, the active ingredient (i.e., a drug for inhibiting or eradicating *H. pylori*) in the drug structure can be released to the site of aggregation of pathogens exactly, thereby enhancing the therapeutic efficacy of the active ingredient.

Test of Drug Release Rate of Drug Structure

First, a solution containing drug structure samples B, C is prepared according to the method of making the drug structure sample. Then, the solution containing drug structure samples B, C undergo a centrifugal concentration process. The resultant concentrate of samples B, C is dipped into a dialysis membrane. Then, the dialysis membrane is placed in a pH 2.5 simulation solution so that the pH value of the concentrate approaches 2.5 gradually. After staying in the pH 2.5 environment for two hours, the dialysis membrane is placed in a pH 6.5 simulation solution so that the pH value of the concentrate approaches 6.5 gradually. After staying in the pH 6.5 environment for two hours, the dialysis membrane is placed in a pH 7.4 simulation solution so that the pH value of the concentrate approaches 7.4 gradually. Afterward, the dialysis membrane stays in the pH 7.4 environment for 44 hours. In the simulation solution at different pH values, the dialysis membrane, which contains the concentrate of samples B, C, is rotated at low speed (in this embodiment, the rotation speed is set to 100 rpm, but the aforesaid low rotation speed is not restrictive of this embodiment.) The aforesaid operating process simulates how samples B, C release a drug in the stomach and gastric mucosa. At different points in time, by high-performance liquid chromatography (HPLC), amoxicillin samples are collected from the simulation solution (of different pH values) where the dialysis membrane containing samples B, C is placed in. Then, concentrations of amoxicillin are detected at a wavelength of 229 nm to therefore measure concentration of the active ingredient released from samples B, C in different pH value environments, and then the concentration is calculated and converted into the release rate.

Figure 7:
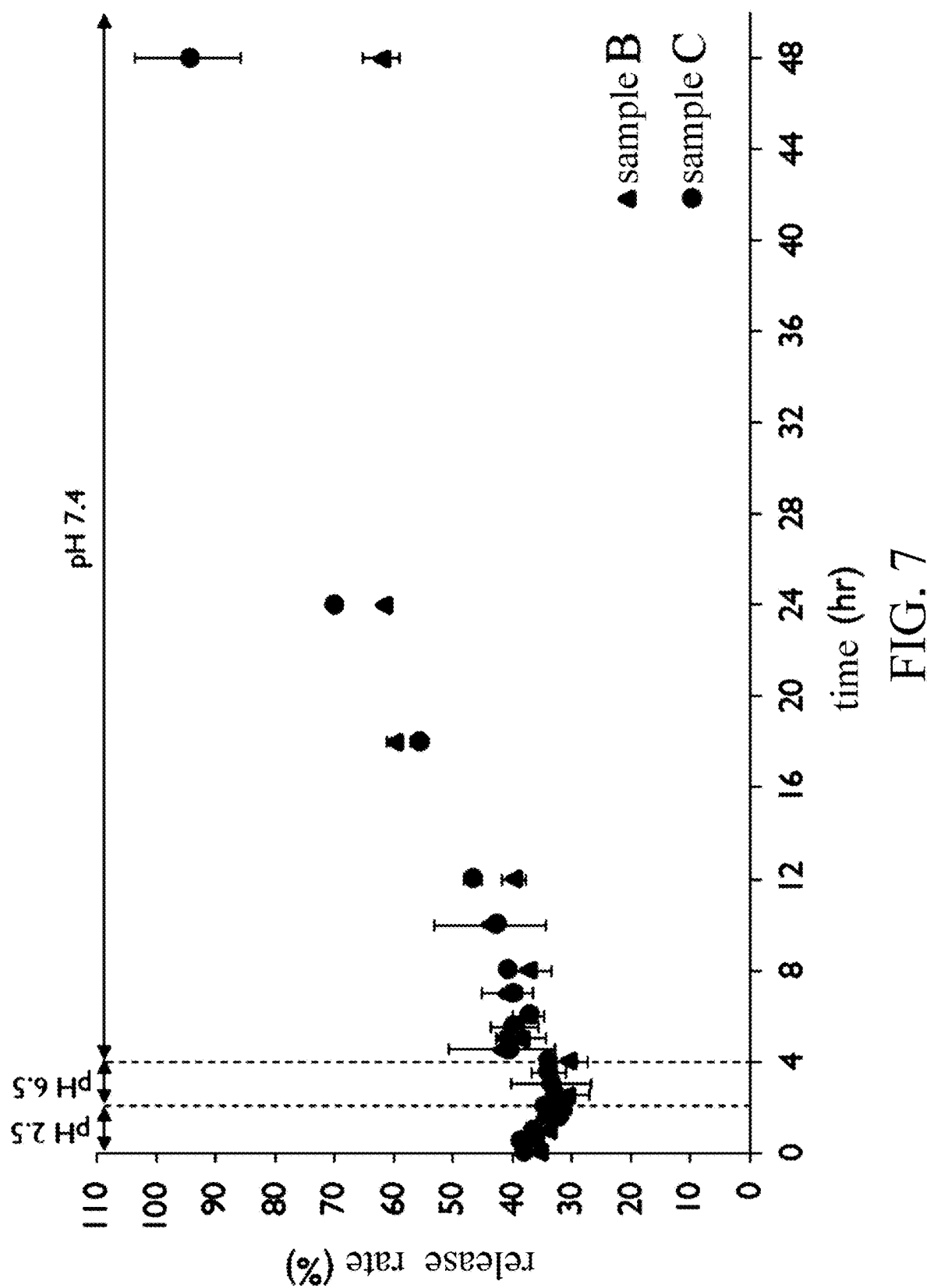
FIG. 7 is a schematic view of the relationship between the release rate of active ingredients from the drug structure and pH value.

The test results are shown in FIG. 7. In the diagram, the release rate of the active ingredient released from drug structure samples B, C increases while the pH value of the environment is approaching a neutral (alkaline) pH value. The experimental results match the situation about how the drug structure is dispersed as a result of the change in charged characteristics of chitosan and observed in FIG. 3 and FIG. 4. Therefore, in this embodiment, the drug structure manifests a satisfactory release rate when located at the inside lining of the stomach. Furthermore, as shown in FIG. 7, the longer the test duration is, the higher (above 90%) is the release rate demonstrated by sample C. It is because the more the negatively charged polymer in the drug structure is, the more it competes with the active ingredient for the positive charges of the chitosan. Hence, the coupled active ingredient is attracted in the drug structure by static electricity and thus can be released more easily.

Test of Capability of Drug Structure to Penetrate Mucus Layer

Figure 8:
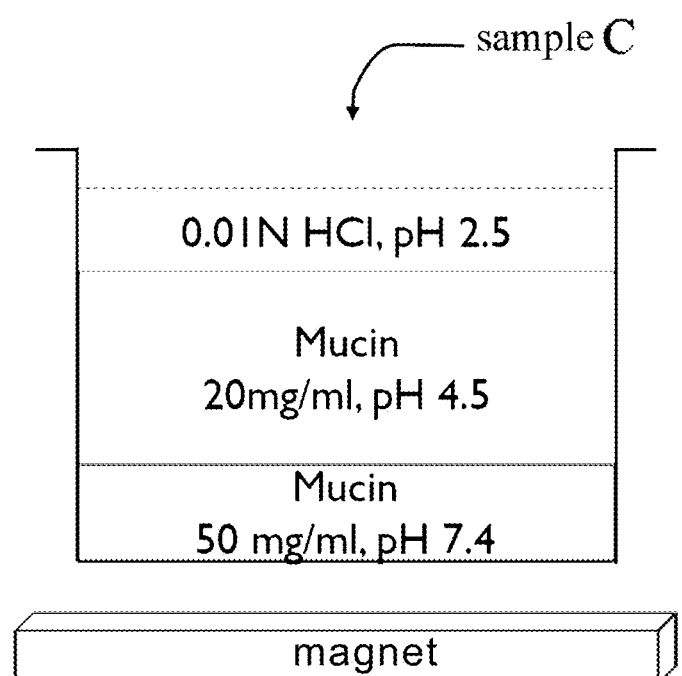
FIG. 8 is a schematic view of a method of testing the capability of the drug structure to penetrate a mucus layer.

First, prepare a simulation mucus layer (shown in FIG. 8) having an upper layer containing 20 mg/ml mucin solution (pH 4.5) and a low layer containing 50 mg/ml mucin solution (pH 7.4) to simulate gastric mucosa mucus layer environment of different depths. The simulation mucus layer is placed in four microcentrifuge tubes, the sample C concentrate which is modified to contain fluorescent substances and concentrated is mixed with 0.01N hydrochloric acid solution (pH 2.5) and then the mixture is slowly introduced into the simulation mucus layer in the four microcentrifuge tubes. The simulation mucus layer of the mixture containing sample C functions as four test samples for use in this test. Afterward, the four test samples are tested under four different test conditions: (1) adding the mixture containing sample C, then applying no magnetic field, but standing still for 5 minutes; (2) adding the mixture containing sample C, then applying a magnetic field, and standing still for 5 minutes; (3) adding the mixture containing sample C, then applying no magnetic field, but standing still for 10 minutes; and (2) adding the mixture containing sample C, then applying a magnetic field, and standing still for 10 minutes. After the four test samples of this test has undergone this test under the aforesaid test conditions, the test samples are frozen and sliced. The sliced frozen test samples are observed under a fluorescent microscope to evaluate distribution of sample C in the simulation mucus layer. By conducting the aforesaid test, it is feasible to further assess the effect of the absence and presence of an applied magnetic field on the capability of the drug structure sample C to penetrate the mucosa. The application of the applied magnetic field is achieved by placing a magnet at the bottom of each microcentrifuge tube (as shown in FIG. 8.)

Figure 9:
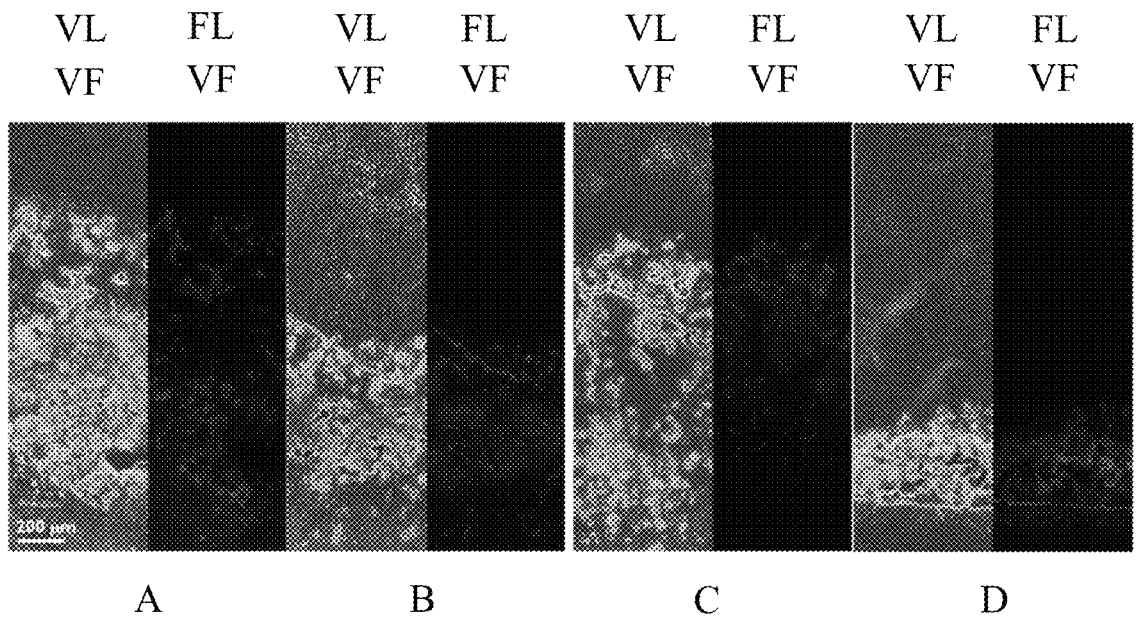
FIG. 9 are schematic views of results of testing the capability of the drug structure to penetrate a mucus layer.
Figure 10:
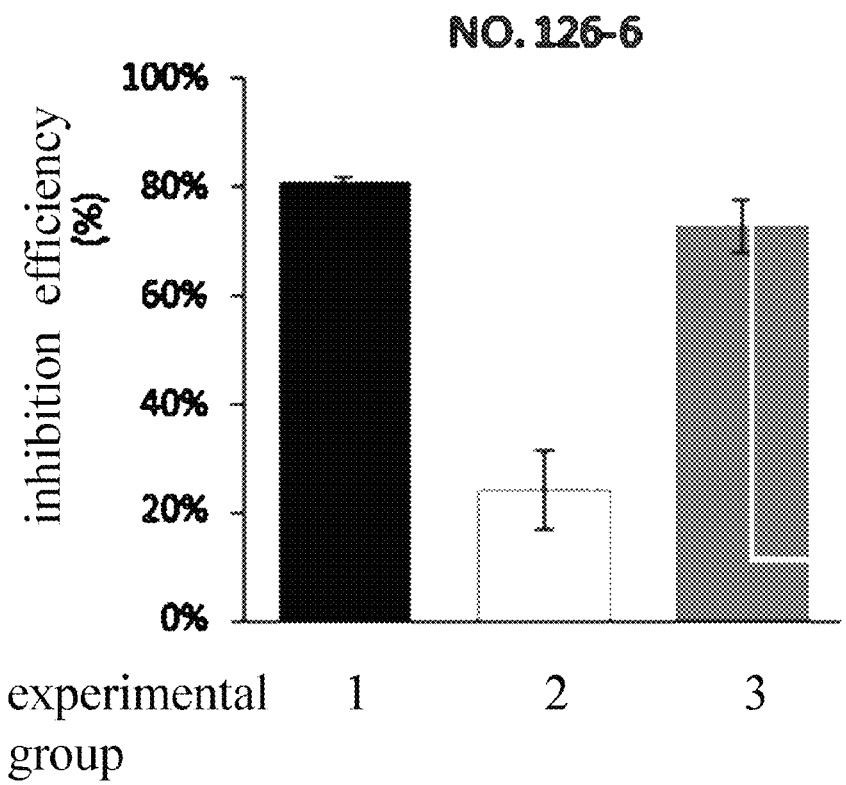
FIG. 10 shows a bar chart of efficiency of inhibition of *H. pylori* by amoxicillin, drug carrier and drug structure.
Figure 11:
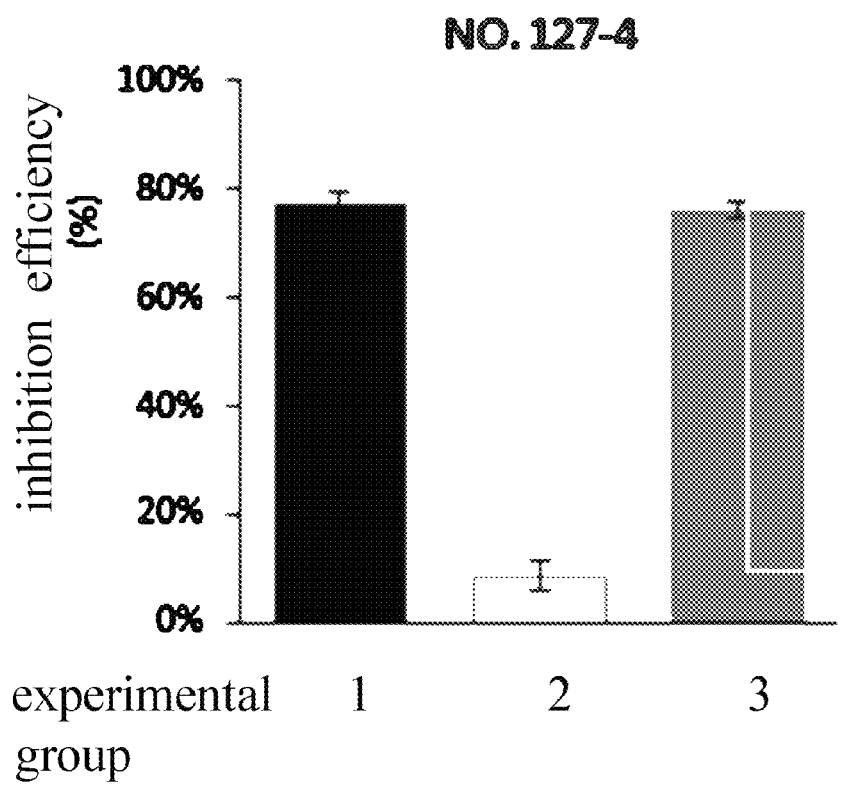
FIG. 11 shows another bar chart of efficiency of inhibition of *H. pylori* by amoxicillin, drug carrier and drug structure.
Figure 12:
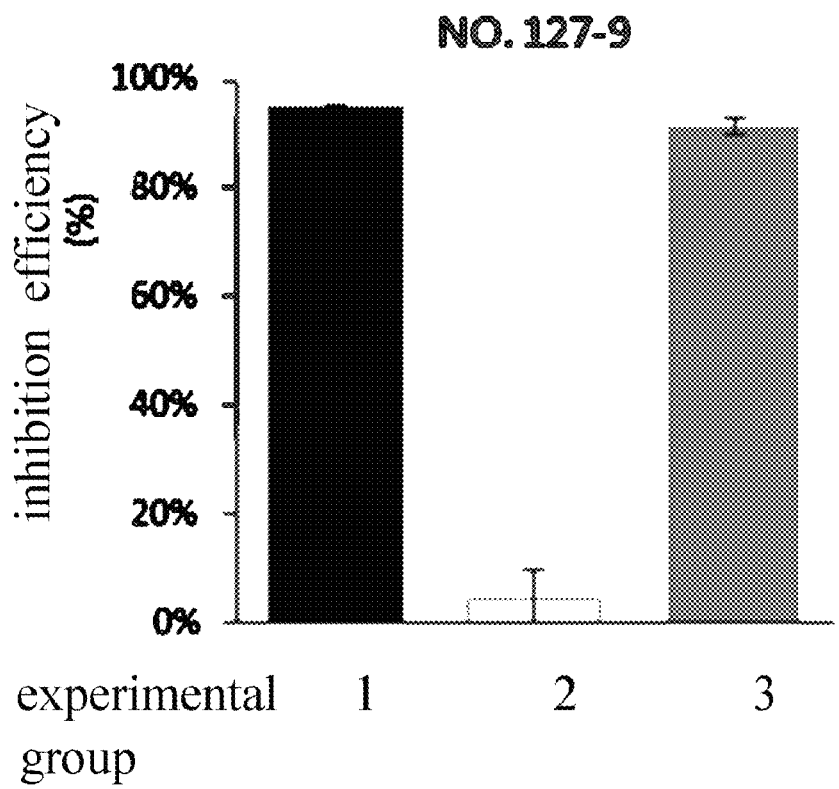
FIG. 12 shows another bar chart of efficiency of inhibition of *H. pylori* by amoxicillin, drug carrier and drug structure.
Figure 13:
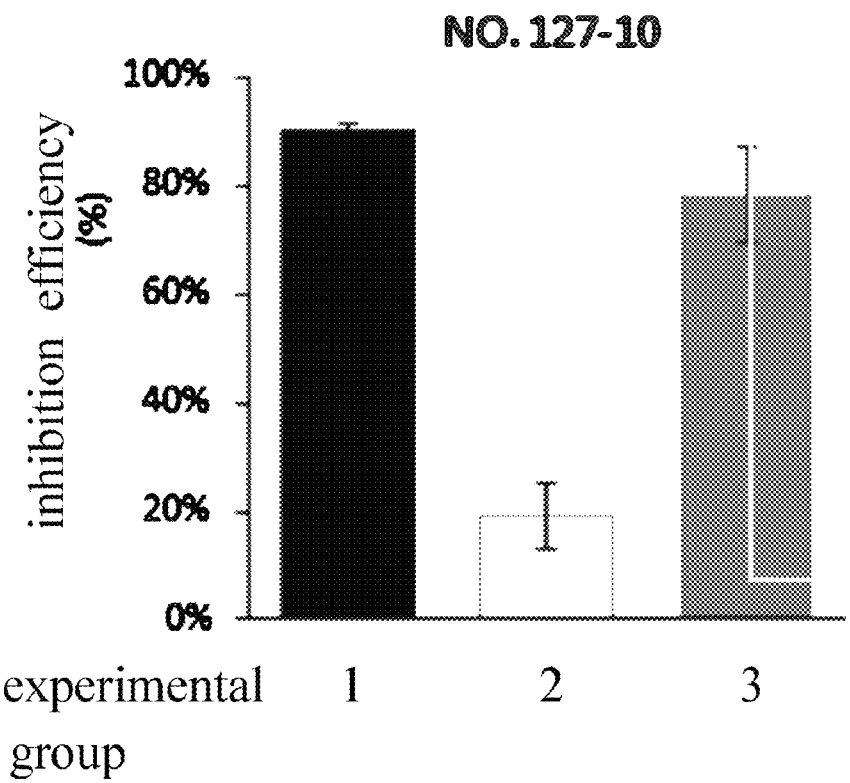
FIG. 13 shows another bar chart of efficiency of inhibition of *H. pylori* by amoxicillin, drug carrier and drug structure.
Figure 14:
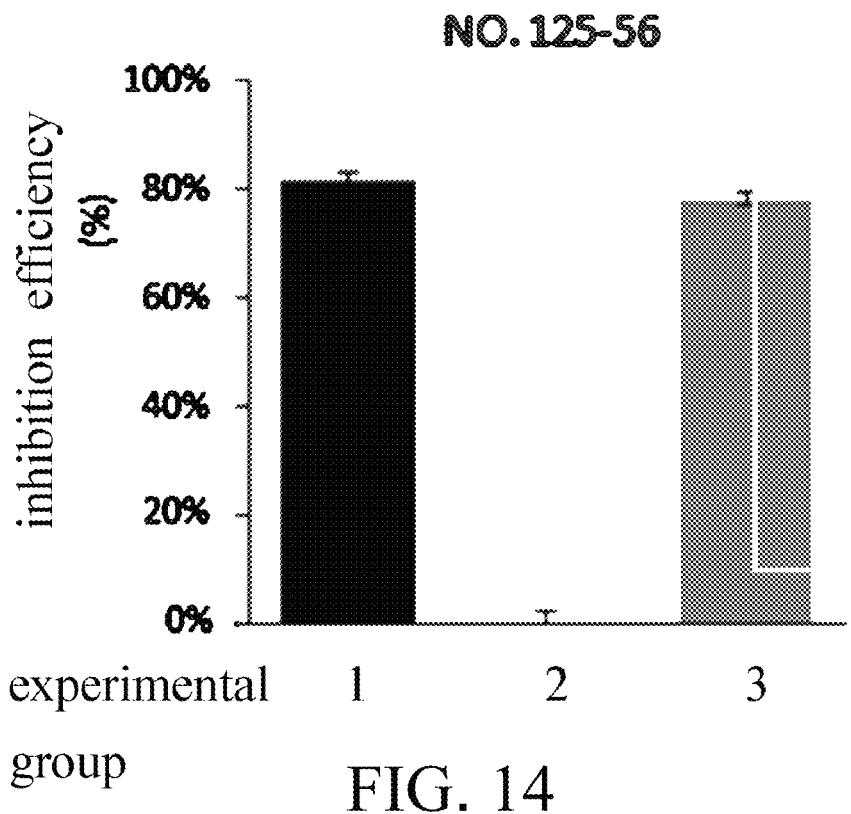
FIG. 14 shows another bar chart of efficiency of inhibition of *H. pylori* by amoxicillin, drug carrier and drug structure.
Figure 15:
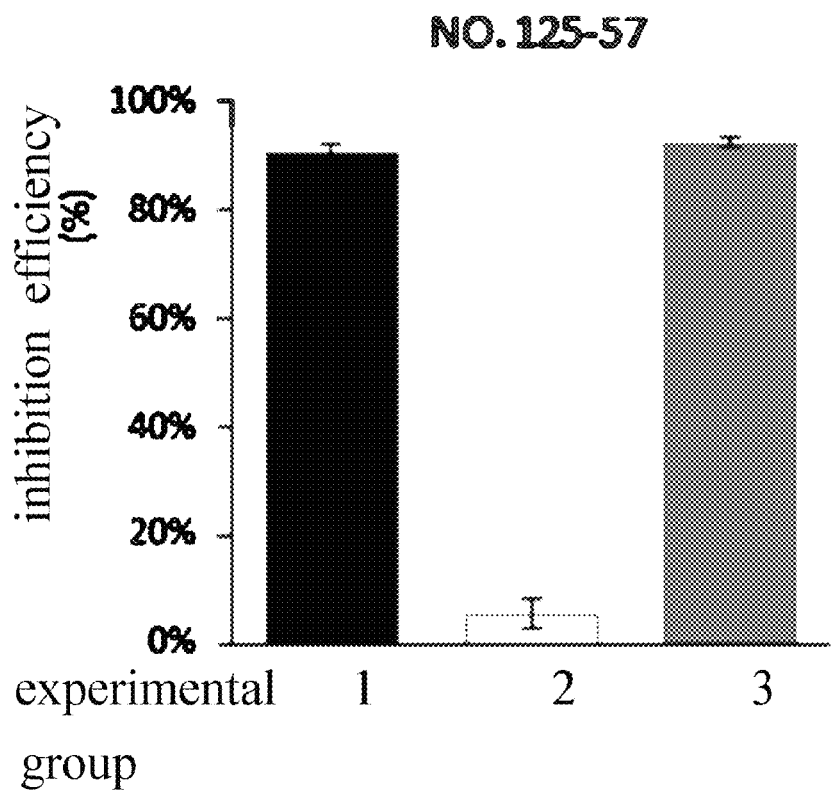
FIG. 15 shows another bar chart of efficiency of inhibition of *H. pylori* by amoxicillin, drug carrier and drug structure.
Figure 16:
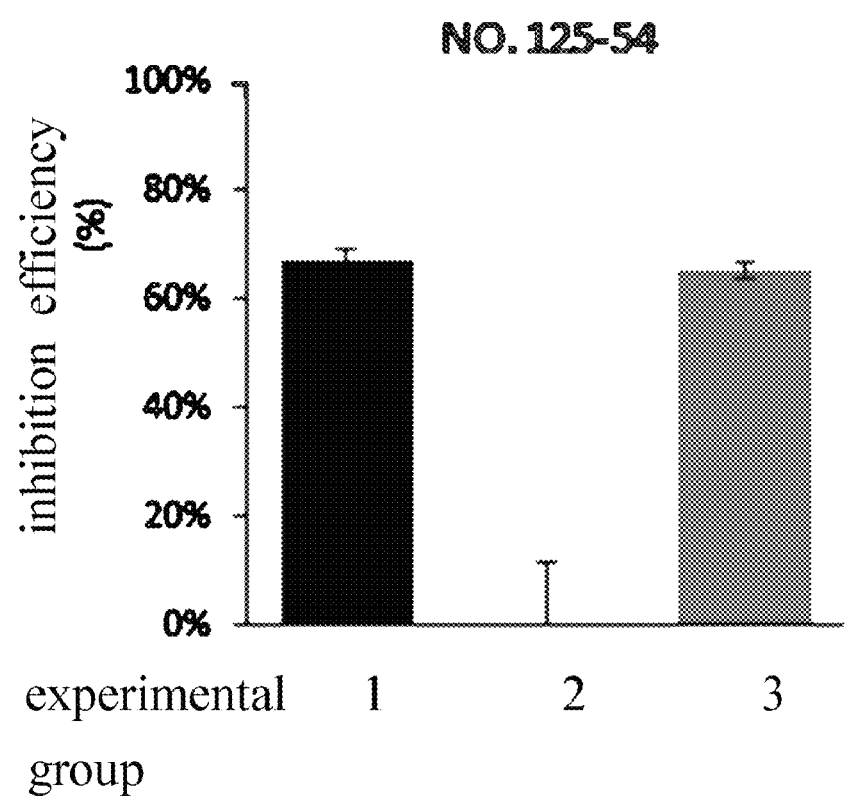
FIG. 16 shows another bar chart of efficiency of inhibition of *H. pylori* by amoxicillin, drug carrier and drug structure.

As shown in FIG. 9, the test results are as follows: the longer the duration of standing still is, the deeper in the mucus layer (i.e., the closer to the bottom thereof) is the drug structure sample C therein; the drug structure sample C is found closer to the bottom of the mucus layer in the presence than absence of the applied magnetic field; and the longer the applied magnetic field lasts, the closer to the bottom of the mucus layer is the drug structure sample C found therein. Given the aforesaid test results, it is inferred that in this embodiment the drug structure can be guided by an applied magnetic field to penetrate the gastric mucosa layer quickly, and thus the drug or active substance in the drug structure penetrate the mucosal layer quickly to therefore release the drug at the site of aggregation of pathogens and kill the pathogens.

Test of Inhibition of *H. Pylori* by Drug Structure

First, bacterial fluids of seven different strains of *H. pylori* are provided. The minimum inhibitory concentrations (MIC) of the bacterial fluids of the seven different strains of *H. pylori* are: 0.016 µg/ml (NO. 126-6), 0.0625 µg/ml (NO. 127-4), 0.0625 µg/ml (NO. 127-9), 0.125 µg/ml (NO. 127-10), 0.25 µg/ml (NO. 125-56), 0.25 µg/ml (NO. 125-57), and 0.5 µg/ml (NO. 125-54). The bacterial fluids of the seven different strains of *H. pylori* are placed in four 15 ml microcentrifuge tubes, respectively. Each microcentrifuge tube contains 5 ml of *H. pylori* bacterial fluid. The four microcentrifuge tubes are defined as experimental group 1, experimental group 2, experimental group 3 and control group, respectively. Then, amoxicillin of the minimum inhibitory concentration is added to experimental group 1 of each strain of *H. pylori*, sample 3 (i.e., drug carrier) of the minimum inhibitory concentration is added to experimental group 2 of each strain of *H. pylori*, sample C (i.e., drug structure) of amoxicillin of the minimum inhibitory concentration is added to experimental group 3 of each strain of *H. pylori*, and nothing is added to the control group. Afterward, experimental groups 1-3 and control group of each strain of *H. pylori* are placed in an incubator to be cultured therein at 37° C., in an anaerobic environment, and for 48 hours. At the end of the 48-hour culturing process, bacterial fluids are extracted from the experimental groups 1-3 and control group of the strains of *H. pylori*, respectively. OD values of the bacterial fluid of the experimental groups and the bacterial fluid of the control group are measured with a spectrophotometer at a wavelength of 450 nm. Then, the OD values are converted into bacterial inhibition rate, so as to analyze amoxicillin, experimental sample 2 not having an active ingredient, and experimental sample C having an active ingredient, for their efficacy of inhibition of *H. pylori*.

As shown in FIGS. 10-16, test results are as follows: since sensitivity to amoxicillin varies from strain of *H. pylori* to strain of *H. pylori*, amoxicillin manifests different degrees of inhibition efficacy toward experimental group 1 of different strains of *H. pylori*. The active ingredient contained in sample C is amoxicillin. As shown in FIGS. 10-16, the presence of sample C has the same inhibitory effect on each strain of *H. pylori* as the sole presence of amoxicillin. As shown in FIGS. 10-16, even the sample 3 which contains no active ingredient has some, albeit small, inhibitory effect on some of the strains of *H. pylori*.

The aforesaid test results indicate that although in this embodiment the drug structure contains only a single active ingredient, it inhibits *H. pylori* effectively. In this embodiment, the drug structure only comprises one of the active ingredients capable of inhibiting *H. pylori*, that is, the drug structure contains only a single ingredient but not any other active ingredient or any auxiliary active ingredient capable of inhibiting *H. pylori* on an auxiliary basis. However, in another embodiment, the drug structure comprises at least two active ingredients or comprise an auxiliary active ingredient, without being limited to this embodiment.

In this embodiment, the auxiliary active ingredient means a substance having auxiliary activity of inhibiting *H. pylori*. The substance having auxiliary activity of inhibiting *H. pylori* does not directly have activity of inhibiting *H. pylori* but assists the active ingredient in functioning well. For example, conventional drugs for treating peptic ulcers include a combination of an antibiotic and a proton-pump inhibitor. The proton-pump inhibitor does not directly have activity of inhibiting *H. pylori* but can enhance the efficacy of antibiotics on an auxiliary basis. Hence, the proton-pump inhibitor is a substance having activity of inhibiting *H. pylori* on an auxiliary basis. In addition to the proton-pump inhibitor, the other auxiliary active ingredients include, for example, an auxiliary active ingredient, such as bismuth.

In this embodiment, the auxiliary active ingredient does not include any substance pharmacologically designed to assist with administration of a drug, improvement of the taste of a drug, or extension of the expiry date of a drug. For instance, in this embodiment, the auxiliary active ingredient does not include: additives commonly for use with drug structures, such as medicine-oriented carriers, flavoring agents, or preservatives.

In this embodiment, there is provided a method of extracorporeal inhibition of *H. pylori*, comprising the steps of: introducing the aforesaid drug structure and administering an effective dose of the drug structure to an *H. pylori* colony. In this embodiment, the method further comprises providing an applied magnetic field and applying it to the drug structure such that the drug structure is capable of specifically inhibiting or even eradicating *H. pylori*. However, in another embodiment, optionally, no magnetic field is applied, without being limited to this embodiment. In this embodiment, the method, optionally, only entails administering the drug structure without administering any other active ingredient or auxiliary active ingredient for inhibiting *H. pylori*, and without using any other means of inhibiting *H. pylori*.

In this embodiment, to inhibit *H. pylori*, the drug structure must be of an effective dose of 1 to 10 mg/kg/day, preferably 3 to 7 mg/kg/day, and most preferably 5 mg/kg/day.

Furthermore, in this embodiment, the drug structure also serves the other purposes, including reducing the required number of instances and the required dosage of taking the drug, alleviating the side-effects of the drug, and enhancing patient compliance.

The drug carrier and drug structure comprises magnetic particles to be guided by an applied magnetic field so as to extend the duration of the retention of the drug structure at the specific sites in the stomach of the human body, assist with the release of the drug from the drug structure, and extend the duration of the retention of the drug structure in the human body. Moreover, the drug carrier and the drug structure are guided by an applied magnetic field to therefore penetrate the gastric mucosal layer quickly, release the drug at the site of aggregation of pathogens, and kill the pathogens. The drug carrier and drug structure further enhance the therapeutic efficacy of the drug structure, so as to reduce the dosage of a drug to take each time and lessen the side-effects of the drug.

Although the present disclosure is disclosed above by preferred embodiments, the preferred embodiments are not restrictive of the scope of the present disclosure. Equivalent changes and modifications made by persons skilled in the art to the preferred embodiments without departing from the spirit of the present disclosure must be deemed falling within the scope of the present disclosure. Accordingly, the legal protection for the present disclosure should be defined by the appended claims.

What is claimed is:

1. A drug carrier, comprising:
   90 to 110 parts by weight of a negatively charged polymer;
   400 to 1250 parts by weight of chitosan; and
   150 to 500 parts by weight of magnetic particles.

2. The drug carrier of claim 1, wherein the negatively charged polymer is of a concentration of 100 parts by weight, the chitosan is of a concentration of 600 to 850 parts by weight, and the magnetic particles are of a concentration of 250 to 350 parts by weight.

3. The drug carrier of claim 1, wherein the drug carrier has a particle diameter of 120 to 200 nm.

4. The drug carrier of claim 1, wherein the drug carrier in an aqueous solution has a surface potential of 45 to 49 mV.

5. The drug carrier of claim 1, wherein the negatively charged polymer is one selected from the group consisting of alginate, heparin, polyacrylic acid, poly (methacrylic acid) and carboxymethyl cellulose.

6. A method of making a drug carrier, comprising steps of:
   (a) providing 90 to 110 parts by weight of a negatively charged polymer solution, 400 to 1250 parts by weight of a chitosan solution and 150 to 500 parts by weight of magnetic particles;
   (b) mixing the negatively charged polymer solution, the chitosan solution and the magnetic particles to form an initial solution; and
   (c) stirring the initial solution for at least 10 minutes to form drug carrier particles.

7. The method of claim 6, wherein the negatively charged polymer is of a concentration of 100 parts by weight, the chitosan is of a concentration of 600 to 850 parts by weight, and the magnetic particles are of a concentration of 250 to 350 parts by weight.

8. A drug structure, comprising:
   90 to 110 parts by weight of a negatively charged polymer;
   400 to 1250 parts by weight of chitosan;
   150 to 500 parts by weight of magnetic particles; and
   500 to 1500 parts by weight of an active ingredient having activity of inhibiting *H. pylori*.

9. The drug structure of claim 8, wherein the negatively charged polymer is of a concentration of 100 parts by weight, the chitosan is of a concentration of 600 to 850 parts by weight, the magnetic particles are of a concentration of 250 to 350 parts by weight, and the active ingredient is of a concentration of 750 to 1000 parts by weight.

10. The drug structure of claim 8, wherein the drug structure has a particle diameter of 137 to 210 nm.

11. The drug structure of claim 8, wherein the active ingredient of the drug structure has a encapsulation efficiency of 72.6 to 79.2%.

12. The drug structure of claim 8, wherein the active ingredient in the drug structure accounts for 30 to 45% (w/w) of a total weight of the drug structure.

13. The drug structure of claim 8, wherein the drug structure in an aqueous solution has a surface potential of 44 to 48 mV.

14. The drug structure of claim 8, wherein the negatively charged polymer is one selected from the group consisting of alginate, heparin, polyacrylic acid, poly (methacrylic acid) and carboxymethyl cellulose.

15. The drug structure of claim 8, wherein the active ingredient is one selected from the group consisting of amoxicillin, clarithromycin, omeprazole, levofloxacin, metronidazole and tetracycline.

* * * * *